(12) United States Patent
Torichigai et al.

(10) Patent No.: US 10,527,588 B2
(45) Date of Patent: Jan. 7, 2020

(54) IMMERSION-TYPE ULTRASOUND FLAW DETECTION DEVICE AND ULTRASOUND FLAW DETECTION SYSTEM

(75) Inventors: Masaaki Torichigai, Tokyo (JP); Mikiyasu Urata, Tokyo (JP); Kiyotaka Aoki, Tokyo (JP); Shinichi Tsuji, Kitakyushu (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 860 days.

(21) Appl. No.: 13/381,450

(22) PCT Filed: Sep. 29, 2010

(86) PCT No.: PCT/JP2010/066930
§ 371 (c)(1),
(2), (4) Date: Dec. 29, 2011

(87) PCT Pub. No.: WO2011/040452
PCT Pub. Date: Apr. 7, 2011

(65) Prior Publication Data
US 2012/0109540 A1    May 3, 2012

(30) Foreign Application Priority Data
Sep. 30, 2009  (JP) .................. 2009-226599

(51) Int. Cl.
*G01N 29/265* (2006.01)

(52) U.S. Cl.
CPC .................. *G01N 29/265* (2013.01)

(58) Field of Classification Search
CPC .......... G01N 29/265; G01N 2291/044; G01N 2291/2636; G01N 29/041
(Continued)

(56) References Cited

U.S. PATENT DOCUMENTS 4,907,314 A * 3/1990 Kershaw .................. 15/104.061
4,964,059 A   10/1990 Sugaya et al.
(Continued)

FOREIGN PATENT DOCUMENTS

JP    62-45167    12/1987
JP    64-50903    2/1989
(Continued)

OTHER PUBLICATIONS

H. Lei, Ultrasonic Pig for Submarine Oil Pipeline Corrosion Inspection, Apr. 2009, Shanghai Jiao University, vol. 45, No. 4, p. 285-291.*

(Continued)

*Primary Examiner* — Michael P Nghiem
*Assistant Examiner* — Dacthang P Ngo
(74) *Attorney, Agent, or Firm* — Wenderoth, Lind & Ponack, L.L.P.

(57) ABSTRACT

An ultrasound flaw detection device which detects abnormalities within a tube while moving in the tube by pressure of water flow. The ultrasound flaw detector includes an ultrasound probe (11) which emits an ultrasound wave from an inside of the tube to a tube wall and receives an echo signal, a pulser-receiver (12) which transmits a pulse signal to the ultrasound probe and to which the received echo signal is inputted, a memory unit (14) which stores the received echo signal, a control unit (15) which controls transmitting timing of the pulse signal from the pulser-receiver to the ultrasound probe and controls writing of the received echo signal to the memory unit, and a power supply unit (19); a flexible member (25) which connects the plurality of parts of the ultrasound flaw detector; and a centering member (26) which keeps the ultrasound probe approximately centered within the tube.

16 Claims, 17 Drawing Sheets

(58) Field of Classification Search
USPC .......................................................... 702/39
See application file for complete search history.

(56) References Cited

U.S. PATENT DOCUMENTS

| | | | | |
|---|---|---|---|---|
| 5,460,046 | A | * | 10/1995 | Maltby et al. .................. 73/623 |
| 6,474,165 | B1 | * | 11/2002 | Harper et al. .................. 73/623 |
| 6,571,634 | B1 | * | 6/2003 | Bazarov et al. ................ 73/623 |
| 2003/0083576 | A1 | * | 5/2003 | Bazarov et al. ............. 600/437 |
| 2013/0068028 | A1 | * | 3/2013 | Hoyt .................... G01N 29/043 |
| | | | | 73/643 |

FOREIGN PATENT DOCUMENTS

| | | |
|---|---|---|
| JP | 3-186759 | 8/1991 |
| JP | 07049336 A * | 2/1995 |
| JP | 9-145687 | 6/1997 |
| JP | 3040641 | 3/2000 |
| JP | 2008-201279 | 9/2008 |

OTHER PUBLICATIONS

G. Short and K. Dawson, Blockage Detection in Long Length of Pipeline Using a New Accoustic Method, Jul. 2009, Pipeline Engineering & Supply Co.*
JP-7049336—Iwamoto Keiichi, Tube Internal Insertion Type Ultrasonic Probe, Published Feb. 1995, English Translation.*
Decision to Grant a Patent dated Jun. 3, 2013 in corresponding Japanese Application No. 2009-226599 (with English translation).
International Search Report dated Nov. 2, 2010 in corresponding International Application No. PCT/JP2010/066930.
International Preliminary Report on Patentability and Written Opinion of the International Searching Authority dated May 18, 2012 in corresponding International Application No. PCT/JP2010/066930.

* cited by examiner

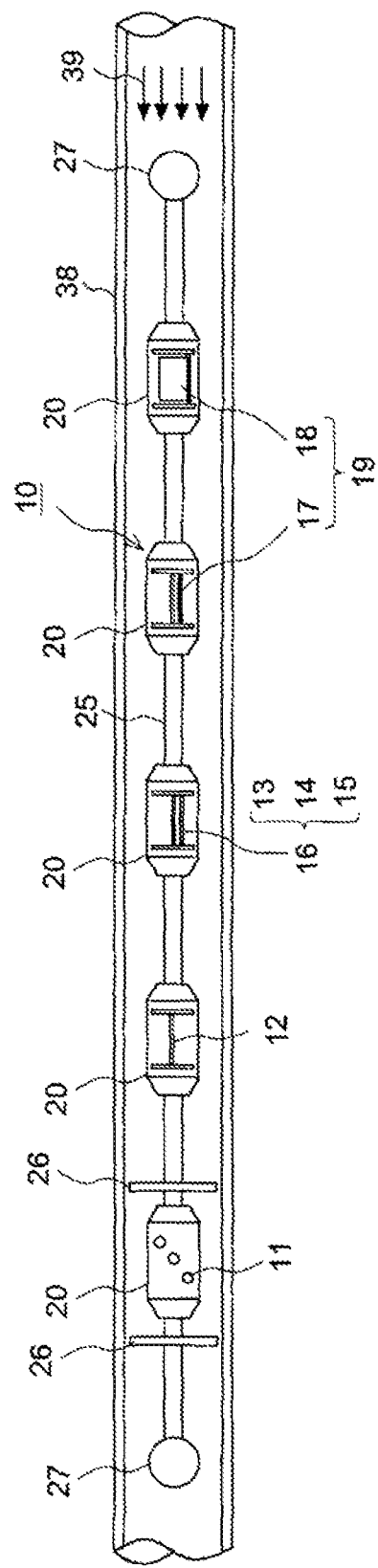

FIG. 2(A)  FIG. 2(B-1) FIG. 2(B-2)
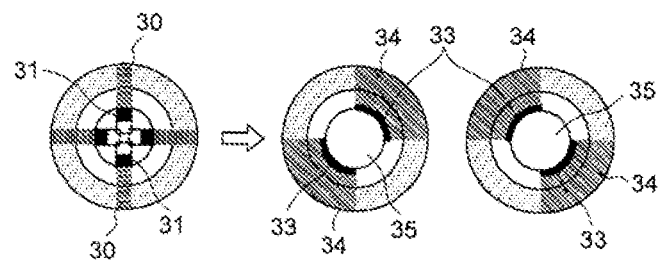
FIG. 3
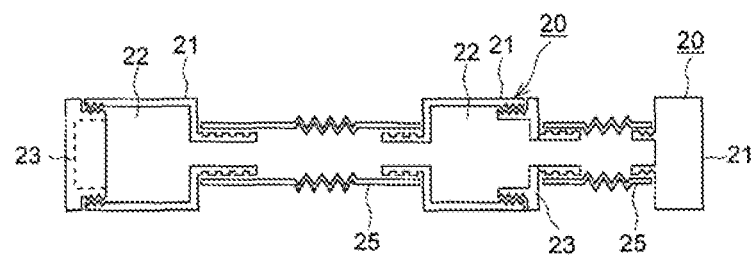

FIG. 19
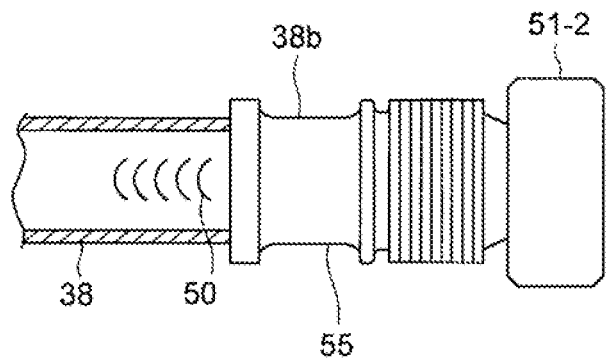
FIG. 20
Soundwave from pulser
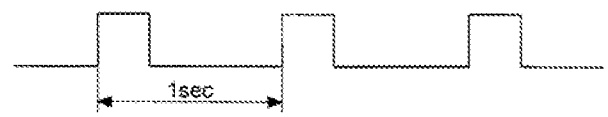
Signal received by
front-side receiver 52-1
Signal received by
rear-side receiver 52-2
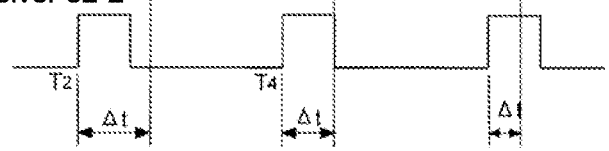

FIG. 21

| Front-side receiver 52-1 | Rear-side receiver 52-2 | $\Delta t$ |
|---|---|---|
| $T_1$ | $T_2$ | $T_1-T_2$ |
| $T_3$ | $T_4$ | $T_3-T_4$ |
| $T_5$ | $T_6$ | $T_5-T_6$ |
| ⋮ | ⋮ | ⋮ |
| $T_n$ | $T_m$ | $T_n-T_m$ |

Related Art

IMMERSION-TYPE ULTRASOUND FLAW DETECTION DEVICE AND ULTRASOUND FLAW DETECTION SYSTEM

BACKGROUND OF THE INVENTION

1. Technical Field

The present invention relates to an ultrasound flaw detection device of an immersion-type and an ultrasound flaw detection system, which is inserted in a tube and is transferred by a pressure of water flow to detect abnormalities within the tube without using a cable for moving the device in a tube, a cable for supplying power or a cable for transmitting and receiving signals.

2. Description of the Related Art

Ultrasound flaw detection devices have been used to detect abnormalities within a tube by nondestructive inspection. For instance, fluid having high temperature and high pressure is introduced to inside of tubes such as a boiler tube in a heat exchanger for a thermal power plant or the like, thereby requiring inspections such as damage, cracks, thinning of the tube. Such tubes in the heat exchanger for the thermal power plant are surrounded by a variety of structures once installed. Thus, it is difficult to perform detection of flaws, flaws or the like inside the tube from the outside of the tube.

As an ultrasound flaw detection device for detecting inside the tube, an immersion-type ultrasound flaw detection probe such as the one disclosed in Japanese Patent No. 3040641 B, is proposed and commercialized. As shown in FIG. 25, an immersion-type ultrasound probe 70 is inserted in a tube 81 by running water and is transferred within the tube 81 by a transferring cable 76. A flexible shaft (elastic material such as a coil spring) 73 is connected to a leading end of the transferring cable 76. An ultrasound probe folder 72 is installed to the flexible shaft 73 and an ultrasound probe 71 is housed in the ultrasound probe folder 72. Damage inside the tube 81 such as wall thinning, scratches, cracks and the like are detected by the ultrasound probe.

In order to keep the ultrasound probe folder centered within the tube 81, a pair of securing rings 78 and 78 of elastic wire is arranged at the front and back of the ultrasound probe folder 72 respectively and a twisted-cage-type centering member 83. The twisted-cage-type centering member 83 has a plurality of elastic wires (a centering member) 77 with both ends thereof amounted separately on the rings at a first specified angle of inclination circumferentially and at a second specified angle of inclination with respect to the shaft center are arranged. The twisted-cage-type centering member 83 is installed with an adjusting nut 80 for adjusting an outer diameter of the centering member 83 smaller than an inner diameter of the tube 81 and a coil spring 79 for keeping approximately the same pressure against the tube wall.

The immersion-type ultrasound probe 70 is pushed into the tube by the transferring cable 76 so as to move in the tube 81 and detect the tube 81. Japanese Unexamined Patent No. 9-145687A discloses a structure of such device. As shown in FIG. 26, such immersion-type ultrasound flaw detection device includes: a guide unit 89 for feeding a coupling type guide rod 90 provided, at the forward end thereof, with an insertion unit 88 into a header 85; a unit 91 for feeding a coil spring 94 coupled with the end of guide rod 90 fed into the header 85 and provided, at the forward end thereof, with a probe head being immersed locally into water into the guide rod 90; an ultrasonic flaw detector 97 (pulser-receiver) connected, respectively, with the end of an ultrasonic flaw detection cable 95 arranged in the coil spring 94 and the end of a water hose 99, and a water pump 98. Since ultrasonic flaw detection can be performed by moving the probe head within the tube by means of water introduced by the water pump 98 and the coil spring 94 fed into the tube by the unit 91 on the inner surface of a boiler tube 86 without cutting the boiler tube and without requiring a large scale machine or enormous volume of water, inspection cost can be reduced significantly.

Japanese Utility Model No. 62-45167 discloses an ultrasound measuring device which is connected to a cable for sending and receiving signals and is installed with a front centering movable member and a rear centering movable member on the front and rear of a main body of the measuring device via a connecter having controllability to hydraulically transfer the ultrasound measuring device smoothly within the tube. A front conical guiding member is provided in front of the front centering member and a rear conical guiding member is provided posterior to the rear centering member. Bottoms of the front and rear conical guiding members face each other so as to receive water pressure efficiently, thereby transferring the ultrasound measuring device efficiently.

SUMMARY OF THE INVENTION

1. Technical Problem

The detection devices disclosed in the prior art publications are configured such that the ultrasound probe is inserted into the tube slowly by means of the transferring cable and water pressure so as to move the ultrasound probe in the tube. To be used in a long tube such as a boiler tube for a heat exchanger, a long transferring cable is required.

In addition to the transferring cable, a power cable for supplying power to the ultrasound flaw detection device in the tube or a signal cable for sending and receiving signals such as a control signal and a echo signal of the detection device are provided, resulting in increased weight of the cables and higher installation cost of the cables. Further, a winding unit for winding the cables is required. With longer cables, the size of the winding unit becomes larger and it is more difficult to handle the device, thereby requiring skilled workers to perform detection of the device.

With more bending sections of the tube, contact resistance with the cable increases. As flow resistance of the cable is large, the water pump requires more power to insert the cable and thus, a bigger water pump is needed.

In view of the above issues, it is an object of the present invention to provide an ultrasound flaw detection device of immersion-type that is inserted into a tube and is capable of moving smoothly within the tube just with water pressure without using a power cable and a signal cable for an ultrasound probe or a cable for transferring the detection device within the tube, as well as an ultrasound flaw detection system.

2. Solution to the Problem

To solve the above problems, as an aspect of the present invention, an ultrasound flaw detection device of an immersion-type that is inserted in a tube and detects abnormalities within the tube while being moved in the tube by pressure of water flow, may include, but is not limited to:

an ultrasound flaw detector which is divided into a plurality of parts and includes: an ultrasound probe which emits an ultrasound wave from an inside of the tube to a tube wall and receives an echo signal to be received that is reflected from the tube wall; a pulser-receiver which transmits a pulse signal to the ultrasound probe and to which the received echo signal is inputted from the ultrasound probe; a memory unit which stores the received echo signal inputted to the pulser-receiver; a control unit which controls a transmitting timing of the pulse signal from the pulser-receiver to the ultrasound probe and controls writing of the received echo signal to the memory unit; and a power supply unit which supplies power to the pulser-receiver;

a flexible member which connects the plurality of parts of the ultrasound flaw detector with each other; and a centering member which keeps the ultrasound probe approximately centered within the tube.

In this manner, the received echo signal inputted to the pulser-receiver is stored in the memory unit, and the control unit controls the transmitting timing of the pulse signal from the pulser-receiver to the ultrasound probe and controls writing of the received echo signal to the memory unit. Both of the controls are performed within the ultrasound flaw detection device of the immersion-type and thus, a cable for sending and receiving signals is not needed.

Further, the power supply unit within the ultrasound flaw detection device supplies power to the pulser-receiver. Thus, a power cable for supplying power is not needed.

The ultrasound flaw detector is divided into a plurality of parts and thus, each divided part of the ultrasound flaw detector can be light-weight and small. As a result, it is possible to move the ultrasound flaw detection device of the immersion-type smoothly through the tube only by the pressure of the water flow of the pressurized water. Thus, a cable for transferring the device is not needed.

According to the above ultrasound flaw detection device of the present invention, it is not necessary to provide a signal cable, a power cable and a transferring cable, resulting in a cableless structure. With the cableless structure, heavy cables, and a cable winder and so on are no longer needed. Thus, it is possible to reduce the size and a production cost of the ultrasound flaw detection device of the immersion-type.

The divided parts of the ultrasound flaw detector are connected one another by the flexible member. Thus, the ultrasound flaw detection device can move smoothly in the tube, even through the bending sections.

The centering member is provided to keep the ultrasound probe approximately centered in the radial direction of the tube. Thus, it is possible to perform the ultrasound flaw detection with high precision.

The control unit may be a single unit performing a variety of controls, or an assembly of more than one control unit which performs each of the different controls.

The received echo signal stored in the memory unit may be extracted by removing the ultrasound flaw detection device out of the tube and then extracting the received echo signal by wire or wireless connection, or by extracting the received echo signal wirelessly while the ultrasound flaw detection device is still in the tube.

It is preferable that the ultrasound probe includes a plurality of transducers that are arranged in a circumferential direction of the tube, and that the pulser-receiver transmits the pulse signal to the plurality of transducers with time interval.

By providing a plurality of transducers in the circumferential direction of the tube, it is possible to cover both of a longitudinal range in the direction of the water flow (the longitudinal direction of the tube) and a circumferential range in the circumferential direction of the tube. Thus, it is possible to perform the ultrasound flaw detection with high precision. In comparison to the case where one transducer is rotated in the circumferential direction to detect flaws, a rotary drive unit is no longer needed, thereby downsizing the device. Further, it is no longer necessary to supply power to the rotary drive unit, thereby downsizing the power supply unit.

Further, the pulser-receiver transmits a pulse signal to the transducers with time interval, thereby requiring fewer pulser-receivers than the transducers (e.g. one pulser-receiver for the transducers). Thus, it is possible to perform ultrasound flaw detection by means of fewer pulser-receivers, resulting in downsizing the pulser-receiver.

Preferably, the ultrasound flaw detector includes an A/D conversion unit which performs A/D conversion of the received echo signal inputted to the pulser-receiver. By this, volume of data stored in the memory unit can be smaller and data processing (signal processing) becomes easier.

Preferably, the control unit is a Field Programmable Gate Array which controls the transmitting timing of the pulse signal from the pulser-receiver to the ultrasound probe and controls the writing of the received echo signal to the memory unit.

FPGA is an integrated circuit in which a variety of logic circuits are integrated in one semiconductor chip in an array form. FPGA can be defined or modified by a user (at a field site) after manufacturing by programming logic circuits. The FPGA may be programmed to control the transmitting timing of the pulse signal by the pulser-receiver (preferably, including preamplifier reception), writing of the received echo signal to the memory unit, and A/D conversion by the A/D conversion unit. As a result, it is possible to downsize the control unit significantly. FPGA may be programmed to perform other controls such as communication control upon receiving data recovery command, in addition to above-described three controls.

It is also preferable that the ultrasound flaw detection device of the immersion-type further includes a float which is fixed to the flexible member and generates buoyancy in the water flow. By this, it is possible to minimize the influence of weight of the ultrasound flaw detector. As a result, the ultrasound flaw detection device can move smoothly in the tube.

It is also preferable that the ultrasound flaw detection device of the immersion-type further includes a whisker-shaped member which is installed to a surface of the ultrasound flaw detector that is along a direction of the water flow. The whisker-shaped member helps the ultrasound flaw detector be more subjected to the pressure of the water flow. As a result, the ultrasound flaw detection device can move smoothly in the tube.

It is also preferable that the ultrasound flaw detection device of the immersion-type further includes a disk which is installed to the flexible member perpendicularly to a direction of the water flow. The disk helps the ultrasound flaw detector be more subjected to the pressure of the water flow. As a result, the ultrasound flaw detection device can move smoothly in the tube.

It is also preferable that the ultrasound flaw detection device of the immersion-type further includes one of a parachute-shaped member and a disk which is connected to one of the divided parts of the ultrasound flaw detector by means of a strip-shaped member. The one of the divided parts of the ultrasound flaw detector is arranged most downstream in a direction of the water flow. The parachute-shaped member or the disk helps the ultrasound flaw detector be more subjected to the pressure of the water flow. As a result, the ultrasound flaw detection device can move smoothly in the tube.

As another aspect of the present invention, an ultrasound flaw detection system may include, but is not limited to:

the above ultrasound flaw detection device of the immersion-type;

an interface unit which is arranged outside of the pipe and is permitted to connect to the memory unit of the ultrasound flaw detection device of the immersion-type; and an output unit which outputs an abnormality detection result of the inside of the tube based on information received from the memory unit via the interface unit.

In this manner, the output unit outputs the abnormality detection result of the inside of the tube based on the information received from the memory unit via the interface unit and thus, it is possible to utilize the data stored in the memory unit. Further, based on the data, a variety of signal processing can be performed to output a desired abnormality detection result easily.

Preferably, the ultrasound flaw detection device of the immersion-type further includes a calculation unit which calculates a wall thickness of the tube wall from a time difference between a first received echo signal reflected from an inner periphery of the tube wall and a second received echo signal reflected from an outer periphery of the tube wall, and the wall thickness of the tube wall having been calculated in the calculation unit is stored in the memory unit, and the stored wall thickness is outputted by the output unit via the interface unit.

In this manner, the wall thickness of the tube wall is calculated in the calculation unit of the ultrasound flaw detection device. Thus, the output unit outside of the tube calculates the wall thickness of the tube without a program and has general-versatility.

The wall thickness of the tube wall and the time difference between the first received echo signal and the second received echo signal are correlated and are convertible into each other. Thus, the time difference alone can be calculated instead of the wall thickness and then stored in the memory unit. The calculation unit may be included in the control unit.

The ultrasound flaw detection system may further include a signal processing unit which receives from the memory unit via the interface unit a first received echo signal that is reflected from an inner periphery of the tube wall and a second received echo signal reflected from an outer periphery of the tube wall, and calculates a wall thickness of the tube wall from a time difference between the first received echo signal and the second received echo signal. Preferably, the wall thickness of the tube wall having been calculated in the signal processing unit is outputted by the output unit.

In this manner, by calculating the wall thickness of the tube wall by the signal processing unit, the calculation unit of the ultrasound flaw detection device is not needed, thereby simplifying the structure of the ultrasound flaw detection device of the immersion-type.

Preferably, the ultrasound flaw detector includes a plurality of transducers that are arranged in a circumferential direction of the tube wall, and the memory unit stores the wall thickness of the tube wall for each of said plurality of transducers, and a smallest value of the wall thicknesses at a plurality of points that correspond to said plurality of transducers is selected, and the selected smallest value is outputted corresponding to a position in a longitudinal direction of the tube.

By selecting the smallest value of the wall thicknesses at the plurality of points that are arranged along the circumferential direction of the tube wall, the most thinning part of the tube wall is used as criteria to detect abnormalities and thinning of the tube wall can be positively detected. Further, by outputting the smallest value of the wall thicknesses corresponding to the positions in the longitudinal direction of the tube, it is easier to determine where the tube wall is thinning.

The position of measuring the wall thickness in the longitudinal direction of the tube is correlated with the measuring time and is convertible with each other. Thus, it is possible to use the measuring time instead of the position in the longitudinal direction of the tube.

The ultrasound flaw detection system may further include a noise processing unit which excludes a wall thickness that corresponds to the first received echo signal having a fluctuation band of a height that exceeds a threshold that is set in advance.

In this manner, the fluctuation of the first received echo signal is calculated. When the calculated fluctuation band exceeds the preset threshold, the wall thickness of the tube wall corresponding to the first received echo signal is excluded. Thus, it is possible to detect abnormalities with high precision by removing the received echo signal which is possibly influenced by the noise.

Preferably, a position in a longitudinal direction of the tube wall that corresponds to the wall thickness is determined from a measuring time of the received echo signal based on a reference echo signal at a characterizing part of the tube wall.

The characterizing part of the tube wall includes a bending section, a butt weld section or the like. An echo signal that is different from the received echo signal reflected from other part of the tube is received at the characterizing part of the tube. The different echo signal reflected from the characterizing part is used as the reference echo signal. The position in the longitudinal direction of the tube wall that corresponds to the wall thickness is determined from the measuring time of the received echo signal based on the reference echo signal at the characterizing part and thus, it is possible to determine the measuring position easily and precisely.

3. Advantageous Effects of the Invention

According to the present invention as described above, it is no longer necessary to provide a signal cable, a power cable and a transferring cable, resulting in a cableless structure. With the cableless structure, heavy cables, a cable winder and so on are no longer needed. Thus, it is possible to reduce the size and the production cost of the ultrasound flaw detection device of the immersion-type.

The divided parts of the ultrasound flaw detector are connected one another by the flexible member. Thus, the ultrasound flaw detection device can move smoothly in the tube, even through the bending sections.

Further, the centering member is provided to keep the ultrasound probe approximately centered in the radial direction of the tube. Thus, it is possible to perform the ultrasound flaw detection with high precision.

BRIEF DESCRIPTION OF THE DRAWINGS

FIG. 1 is a side view of an ultrasound flaw detection device of an immersion-type in relation to a preferred embodiment of the present invention.

FIG. 2 is a schematic view illustrating positions of belt-type plastic transducers which are used for an ultrasound probe.

FIG. 3 is a sectional view of a waterproof member and a flexible shaft.

FIG. 19 is a side view of a boiler tube equipped with a sound wave transmitter.

FIG. 20 is a frame format of sound wave information and received signal information.

FIG. 21 is a diagram showing reception results and measuring positions.

DETAILED DESCRIPTION OF THE INVENTION

Figure 4:
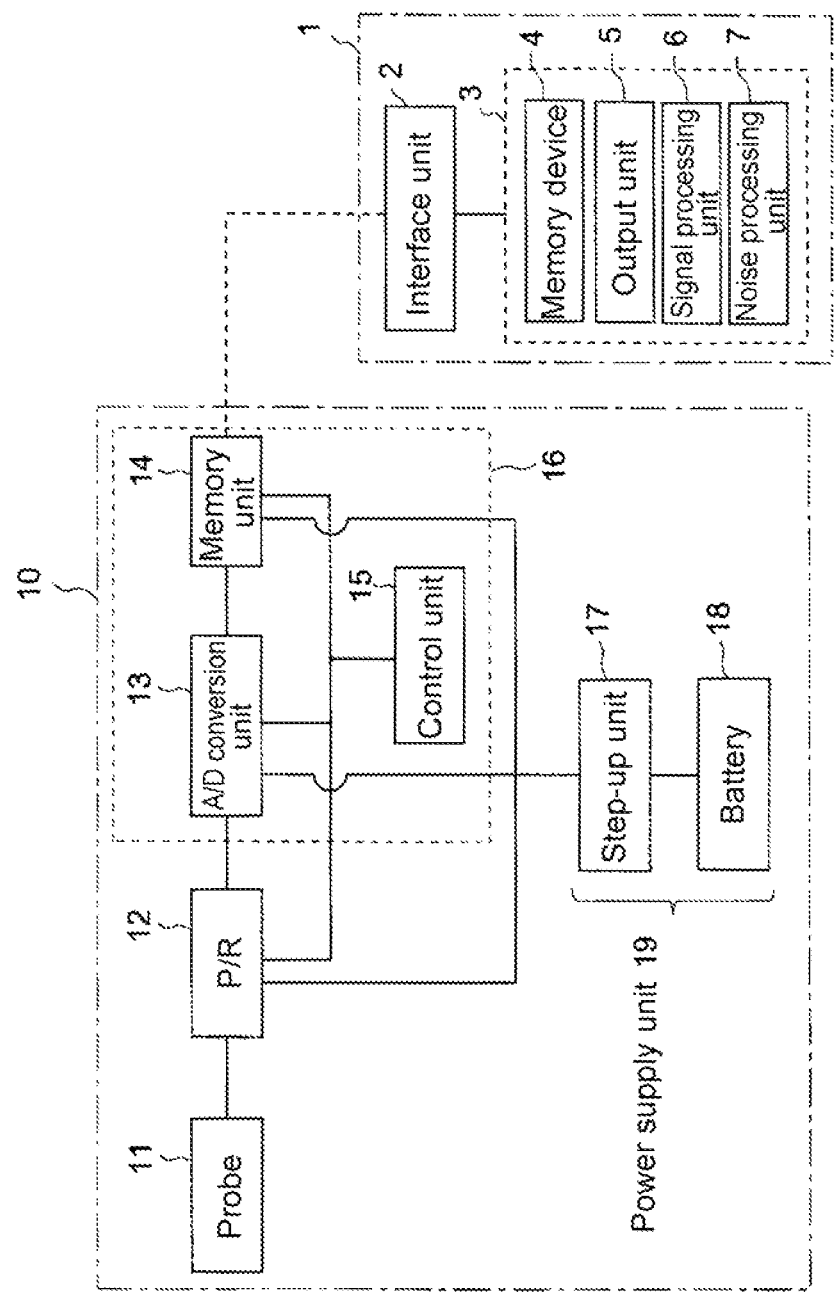
FIG. 4 is a block diagram of the ultrasound flaw detection device in relation to a preferred embodiment of the present invention.

A preferred embodiment of the present invention will now be described in detail with reference to the accompanying drawings. It is intended, however, that unless particularly specified, dimensions, materials, shape, its relative positions and the like shall be interpreted as illustrative only and not limitative of the scope of the present invention.

FIG. 1 is a side view of an ultrasound flaw detection device of an immersion-type in relation to a preferred embodiment of the present invention.

The ultrasound flaw detection device of the immersion-type moves within a tube 38 through the water flow 39 which is formed by pressurized water introduced into the tube (tube wall) 38 from a water pump (not shown) to detect abnormalities in the tube 38. The ultrasound flaw detection device of the immersion-type performs ultrasound flaw detection without using a cable for moving the device in the tube 38 such as a coil spring, a cable for supplying power and a cable for transmitting and receiving signals.

The ultrasound flaw detection device of the immersion-type mainly includes an ultrasound flaw detector which is divided into a plurality of parts and includes an ultrasound probe (sensor) 11, a pulser-receiver 12, a PC unit 16 having an A/D conversion unit 13, a memory unit 14 and a control unit 15, a power supply unit 19 having a step-up circuit 17 and a battery 18, a waterproof member 20 housing each of the plurality of parts of the ultrasound flaw detector, a flexible shaft 25 which connects the plurality of parts of the ultrasound flaw detector with each other and a centering member 26 which keeps the ultrasound probe approximately centered within the tube 38 in a radial direction of the tube 38.

The ultrasound probe 11 transmits ultrasound wave to the tube wall 38 upon application of a pulse signal. Once receiving an echo signal reflected from the tube wall 38, the ultrasound probe 11 outputs a received echo signal depending on strength of the ultrasound wave. The ultrasound probe 11 includes a sound/electricity reversible conversion element. The ultrasound probe may include at least one of an electrostrictive element and a magnetostrictive element, or at least one of transducers formed by a combination of an electrostrictive element and a magnetostrictive element or the like.

When using the ultrasound probe 11 having a plurality of transducers, the transducers 31 are preferably disposed from one another in a circumferential direction of the tube wall 38 as shown in FIG. 2A.

The ultrasound flaw detection device of the immersion-type is moved in the tube 38 merely by the pressure of the water flow and thus, it is difficult to control the position of the ultrasound probe 11. However, a plurality of transducers 31 are arranged circumferentially in the tube wall 38 resulting in providing a plurality of scanning ranges 30 in the circumferential direction of the tube 38. As a result, it is possible to detect abnormalities in the circumferential direction of the tube wall 38 without turning the ultrasound probe 11. In comparison to the case where one transducer is rotated in the circumferential direction to detect flaws, a rotary drive unit is no longer needed, thereby downsizing the device. Further, it is no longer necessary to supply power to the rotary drive unit, thereby resulting in downsizing of the power supply unit.

Preferably, the pulser-receiver transmits a pulse signal to the transducers with time interval, thereby requiring fewer pulser-receivers 12 relative to the transducers (e.g. one pulser-receiver 12 for the transducers). Thus, it is possible to perform ultrasound flaw detection by means of fewer pulser-receiver 12, resulting in downsizing of the pulser-receiver 12.

In the case where more than one transducer is provided, it is preferable to use belt-type plastic transducers 33 as shown in FIG. 2B-1 and FIG. 2B-2. The belt-type plastic transducer has plastic property and is bendable along a curved surface. For instance, as shown in the drawings, four belt-type plastic transducers 33 are arranged with such curvature as to fit along the central part 35 of the ultrasound probe 11 and a scanning range 34 of each transducer 33 is set to 90° so as to scan 360° around the central part 35 at a time. For convenience in explaining the structure, the belt-type plastic transducers 33 are divided into two parts and separately illustrated in FIG. 2B-1 and FIG. 2B-2. In reality, four belt-type plastic transducers 33 are arranged at 90° from one another around the central part 35. The drawings illustrate the case where four transducers 33 are provided. However, this is not limitative and the number of the belt-type transducers 33 is adjustable depending on a corresponding angle.

In reference to FIG. 1, the pulser-receiver 12 transmits the pulse signal. The pulser-receiver 12 applies the pulse signal to the ultrasound probe 11 and receives the echo signal (received echo signal) from the ultrasound probe 11. The pulser-receiver 12 includes a signal transmitting part for transmitting the pulse signal and a signal receiving part for receiving the echo signal. The signal transmitting part includes, for instance, a pulse generator with a clock generator for generating a primitive signal inside and outputs a pulse signal of a frequency represented in a preset frequency data based on a frequency of the primitive signal, a delay circuit which provides a delay in the generated pulse signal to each of the transducers and an amplifier circuit which converts the delayed pulse signal into high voltage and applies the high voltage to the ultrasound probe 11. These parts are controlled by the control unit 15. In the case of using the ultrasound probe 11 with more than one transducer, the pulser-receiver 12 having a corresponding number of channels is used.

The drawings show the PC unit 16 configured such that the A/D conversion unit 13, the memory unit 14 and the control unit 15 are mounted on a single circuit board. However, this is not limitative and the A/D conversion unit 13, the memory unit 14 and the control unit 15 may be mounted on separate circuit boards or two of the units may be mounted. Alternatively, the PC unit 16 may be configured without the A/D conversion unit 13.

The A/D conversion unit 13 converts the received echo signal received by the pulser-receiver 12 from analog waveforms to digital waveforms.

The memory unit 14 stores the received echo signal having been converted to digital waveforms by the A/D conversion unit 13. In the case where the A/D conversion unit 13 is not provided, the memory unit 14 may store analog waveforms of the received echo signal.

The control unit 15 controls the transmitting of the pulse signal by the pulser-receiver 12 and the writing of the received echo signal to the memory unit 14, at the very least. The control unit 15 may be a single unit performing a variety of controls, or an assembly of more than one control unit 15 which performs each of the different controls.

For instance, the control unit 15 may control A/D conversion of the A/D conversion unit 13 or the like. It is preferable to use a FPGA (Field Programmable Gate Array) that allows a single control unit 15 to perform the above controls. FPGA is an integrated circuit in which a variety of logic circuits are integrated in one semiconductor chip in an array form. FPGA can be defined or modified by a user after manufacturing by programming logic circuits. The FPGA may be programmed to control the transmitting timing of the pulse signal by the pulser-receiver 12 (preferably, including preamplifier reception), writing of the received echo signal to the memory unit 14, and A/D conversion by the A/D conversion unit 13. As a result, it is possible to downsize the control unit 15 significantly. FPGA may be programmed to perform other controls such as communication control upon receiving data recovery command, in addition to above-described three controls.

The power supply unit 19 includes the step-up circuit 17 and the battery 18. The step-up circuit 17 distributes power of the battery 18 to the pulser-receiver 12 and the PC unit 16. The battery 18 may be provided with a power switch which turns on and off the power supply.

The above ultrasound flaw detector is divided into a plurality of parts each being housed in the waterproof member 20. FIG. 1 illustrates an exemplary case in which the ultrasound flaw detector is divided into the ultrasound probe 11, the pulser-receiver 12, the PC unit 16, the step-up circuit 17 and the battery 18. However, this is not limitative. The diameter of the waterproof member 20 is set based on the diameter of the tube 38 which is an object to be detected, the ultrasound flaw detector may be divided into parts as desired so that each divided part can be housed in the waterproof member 20.

As shown in FIG. 3, the waterproof member 20 may be made of a material lighter than water such as PP resin and be shaped into a round shape, an oval shape or a polygonal column shape to seal the air inside as a waterproof structure. By this, the ultrasound flaw detection device of the immersion-type is carried afloat in the water and thus, friction is unlikely to be generated on the inner surface of the tube 38 even with projections or the like.

The waterproof member 20 has a container part 21 having a space 22 for storing the divided part of the ultrasound flaw detector, and a cover 23 for closing an open end of the container part 21. The space 22 of the container part 21 is sealed by the cover 23 to prevent the water from entering.

The waterproof members 20 are connected by a flexible shaft 25 one another.

The flexible shaft 25 is made of flexible material such as flexible rubber including PVC. The flexible shaft 25 may have a threaded part to be connected to the divided part of the waterproof member and may have a waterproof structure.

As shown in FIG. 1, a centering member 26 keeps the ultrasound probe 11 approximately centered in the radial direction of the tube 38. The drawing shows a pair of centering members 11 provided on the front and back of the waterproof member 20 having the ultrasound probe 11 stored inside. However, this is not limitative; the centering member may be provided adjacent to another one of the waterproof members 20. The centering member 26 may be a twisted-cage-type centering member illustrated in FIG. 25, having a plurality of elastic wires.

It is also possible to provide a tip guide 27 on an end of the flexible shaft 25. The tip guide 27 has an inclined or round surface with respect to a vertical surface in a traveling direction of the ultrasound flaw detection device of immersion-type. The inclined or round surface of the tip guide 27 allows the ultrasound flaw detection device to travel smoothly in the tube 38 when passing the bending sections of the tube 38.

In this manner, the echo signal received by the pulser-receiver 12 is stored in the memory unit 14 and the transmitting timing of the pulse signal and writing of the received echo signal are performed by the control unit 15. All these are performed in the ultrasound flaw detection device. Thus, a signal cable for sending and receiving signals is no longer needed.

Further, supplying of the power to the pulser-receiver 12 is performed by a power supply unit 19 in the ultrasound flaw detection device. Thus, a power cable for supply electric power is no longer needed.

The ultrasound flaw detector is divided into a plurality of parts and each divided part is stored in one of the waterproof members 20. It is possible to reduce the weight and size of the waterproof member 20 and thus, the ultrasound flaw detection device can be transferred in the tube only by pressure of the water flow of the pressurized water. As a result, it is possible to provide a cableless structure of the ultrasound flaw detection device.

According to the ultrasound flaw detection device of the immersion-type of the preferred embodiment, it is not necessary to provide a signal cable, a power cable and a transferring cable, resulting in a cableless structure. By not using a cable, heavy cables, and a cable winder and so on are no longer needed. Thus, it is possible to reduce the size and the production cost of the ultrasound flaw detection device of the immersion-type.

The divided parts of the ultrasound flaw detector are connected one another by the flexible shaft 25. Thus, the ultrasound flaw detection device can move smoothly in the tube, even through the bending sections.

The centering member 26 is provided to keep the ultrasound probe 11 approximately centered in the radial direction of the tube 38. Thus, it is possible to perform the ultrasound flaw detection with high precision.

A signal flow of the ultrasound flaw detection device and a structure of an external device 1 provided outside the tube in relation to the preferred embodiment are explained in reference to FIG. 4. FIG. 4 describes a function of each device.

First, the pulser-receiver 12 transmits the pulse signal to the ultrasound probe 11. The pulser-receiver 12 is controlled by the control unit 15. In the case of having a plurality of channels, the pulser-receiver 12 transmits the pulse signal for each of the channels in time-multiplexed manner. The ultrasound probe 11 emits an ultrasound wave from the transducer of each channel to the tube wall. The received echo signal reflected from the tube wall 38 is received by the transducer of each channel.

The received echo signal of each of the channels received by the ultrasound probe 11 is then inputted to the pulser-receiver 12 sequentially and amplified.

Then, A/D conversion unit 13 performs A/D conversion of the received echo signal having been amplified. The received echo signal having been converted represents an echo height. The echo height and channel information corresponding to the echo height are stored in the memory unit 14. The memory unit 14 may also store wall thickness data of the tube wall 38. The wall thickness of the tube wall 38 is obtained from a time difference between a first received echo signal S1 reflected from an inner periphery of the tube wall 38 and a second received echo signal B1 reflected from an outer periphery of the tube wall 38.

Figure 5:
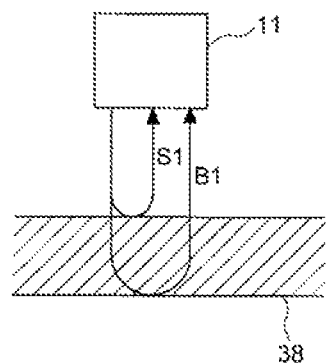
FIG. 5 is an explanatory view of a first received echo signal and a second received echo signal.
Figure 6:
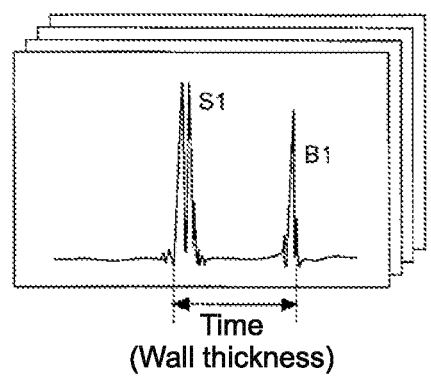
FIG. 6 describes waveforms of the first received echo signal and the second received echo signal.

As shown in FIG. 5 and FIG. 6, the reception time difference between the first received echo signal S1 and the second received echo signal B1 corresponds to the wall thickness of the tube 38. Thus, the time difference between the first received echo signal S1 and the second received echo signal B1 may be stored in the memory unit as the wall thickness data. Alternatively, the time difference between the first received echo signal S1 and the second received echo signal B1 may be converted to the wall thickness and the data of the wall thickness may be stored. The first received echo signal S1 and the second received echo signal B1 are obtained in the manner below. A threshold is set in advance in a measuring gate circuit. An echo signal above the threshold is inputted to a measurement clock (counter). When detecting the echo signals over the threshold twice (S1 and B1), the measurement clock counts the number of clock ticks between the received echo signal of the first time and the received echo signal of the second time. The number of clock ticks corresponds to the wall thickness of tube 38. In the case where the wall thickness is obtained from the time difference between the first received echo signal S1 and the second received echo signal, a calculation unit (not shown) may be provided in the ultrasound flaw detection device of the immersion-type. The calculation unit may be provided in the control unit 15.

When the analog-digital conversion is performed by the A/D conversion unit 13, writing of the received signal to the memory unit 14 is controlled by the control unit 15. The electric power from the battery 18 is distributed by the step-up circuit 17 and supplied to the pulser-receiver 12, the A/D conversion unit 13 and the memory unit 14.

After performing the ultrasound flaw detection, the data stored in the memory unit 14 is moved to the external device 1. The external device 1 includes an interface unit 2 and an external processing unit 3.

The interface unit 2 recovers the data stored in the memory unit 14 and sends the recovered data to the external processing unit 3. The interface unit 2 may be installed with a data-recovery communication software.

The data is recovered from the memory unit 14 by wire or wireless connection. Specifically, the ultrasound flaw detection device of the immersion-type includes a connector that is connected to the memory unit such as to allow data communication with the memory unit 14. The connector is connected to the interface unit 2 so as to recover data from the memory unit 14. The connector may be provided indirectly to the memory unit 14 and may be provided in the battery 18. In such case, a data cable is provided to send and receive the data between the memory unit 14 and the connector of the battery 18.

The external processing unit 3 includes a memory device 4, an output unit 5, a signal-processing unit 6 and a noise-processing unit 7. The external processing unit 3 is formed by a micro computer having a CPU, a ROM, a RAM, an I/O interface, a display and the like, which perform functions of the above devices of the external processing unit 3.

The memory device 4 stores the data recovered from the memory unit 14 of the ultrasound flaw detection device. The memory device 4 may also store calculation results from the signal-processing unit 6 and the noise-processing unit 7.

The output unit 5 outputs a result of abnormality detection in the tube 38 based on the data recovered from the memory unit 14 via the interface unit 2. The result of abnormality detection to be outputted may be the data stored in the memory unit 14 or the data having been process as described above. Preferably, the output unit 5 outputs an image of the wall thickness distribution corresponding to a position in a longitudinal direction of the tube 38.

The signal-processing unit 6 performs a variety of calculation based on the data stored in the memory device 4, e.g. calculations (1) to (3) described below.

Calculation (1)

The measuring position of the received echo signal in the longitudinal direction of the tube 38 is obtained.

The measuring position may be obtained by a position information recognition unit that is provided in the ultrasound flaw detection device. The position information recognition unit is shown in FIG. 17 to FIG. 24 and described later.

Alternatively, the position in the longitudinal direction of the tube 38 that corresponds to the wall thickness may be determined from a measuring time of the received echo signal based on a reference echo signal at a characterizing part of the tube wall 38. The characterizing part of the tube wall 38 includes a bending section, a butt weld section or the like. An echo signal, different from the received echo signal reflected from other part of the tube 38, is received at the characterizing part of the tube 38. The different echo signal reflected from the characterizing part is used as the reference echo signal. The echo signal may not be received at the bending section. In such case, the reference echo signal includes an echo signal of a no-reception state.

The reference echo signal is extracted from the received echo signals of measured time series, and from a position where the reference echo signal is measured, a position of the received echo signal in the longitudinal direction of the tube 38 can be obtained based on a traveling speed of the ultrasound flaw detection device. In the case where a plurality of reference echo signals are detected, the position of the received echo signal in the longitudinal direction can be obtained by assigning the received echo signals equally among a plurality of characterizing parts.

Calculation (2)

The time difference between the first received echo signal and the second received echo signal is calculated and converted to the wall thickness of the tube wall 38. The wall thickness is outputted to the output unit 5, corresponding to the position in the longitudinal direction of the tube 38.

Calculation (3)

In the case where the ultrasound flaw detector has more than one channel, a smallest value of the wall thicknesses at a plurality of points that are arranged along the circumferential direction of the tube wall 38 and correspond to the plurality of transducers arranged in the circumferential direction. The selected smallest value is outputted to the output unit 5, corresponding to a position in the longitudinal direction of the tube 38.

In this manner, the wall thickness of the tube wall 38 is calculated in the signal-processing unit 6 of the external device 1. Thus, a calculation unit of the ultrasound flaw detection device is not needed, thereby simplifying the structure of the ultrasound flaw detection device of the immersion-type.

By selecting the smallest value of the wall thicknesses at the plurality of points that are arranged along the circumferential direction of the tube wall 38, the most thinning part of the tube wall 38 is used as criteria to detect abnormalities and thinning of the tube wall 38 can be positively detected. Further, by outputting the smallest value of the wall thicknesses corresponding to the position in the longitudinal direction of the tube 38, it is easier to determine where the tube wall 38 is thinning.

The noise-processing unit 7 removes noise from the received echo signal having been measured. Specifically, the first received echo signal inputted to the pulser-receiver 12 has a height which corresponds to received voltage. The height of the first received echo signal is stored in the memory unit 15 in time series. For instance, when there is a scale or the like on the inner surface of the tube 38, the height of the first received echo signal is low. Then, the noise processing unit 7 excludes a wall thickness corresponding to the first received echo signal having a fluctuation band of a height that exceeds a preset threshold in the same manner as the case where the height of the first received signal is below the preset threshold. It is also possible to perform the noise processing based on a fluctuation band of the second received echo signal instead of the first received echo signal.

After performing the noise processing by the noise-processing unit 7, the signal-processing unit 6 may preferably perform a variety of processing.

In this manner, the fluctuation of the first or second received echo signal is calculated. When the calculated fluctuation band exceeds the preset threshold, the wall thickness of the tube wall 38 corresponding to the first and second received echo signals is excluded. Thus, it is possible to accurately detect abnormalities by removing the received echo signal that corresponds to the noise.

Further, the external processing unit 3 may include a calibration function, an A-scope mode display function, a thickness display function, a measurement start command function, a measurement finish command function and a data recovery command function.

One exemplary case of the ultrasound flaw detection device of the immersion-type and the ultrasound flaw detection system in relation to the preferred embodiment is explained above. However, the present invention is not limited to this. While the present invention has been described with reference to an exemplary case, it will be obvious to those skilled in the art that various changes may be made without departing from the scope of the invention.

Modifications of the preferred embodiment are described below. First through tenth modifications have structures that facilitate movement of the ultrasound flaw detection device by the pressure of the water flow. An eleventh modification has a structure having a position information recognition unit that detects a position of the received echo signal in the longitudinal direction of the tube 38.

First Modification

Figure 7:
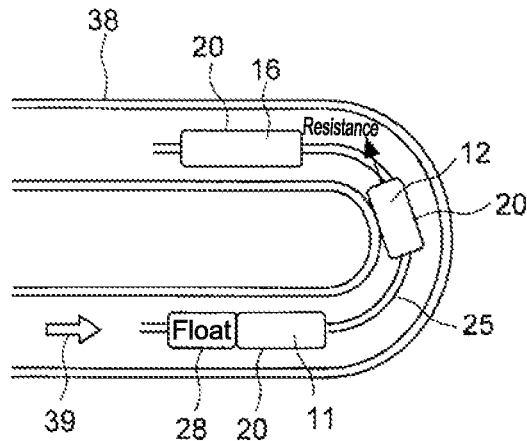
FIG. 7 is a partial side view of the ultrasound flaw detection device to which a float is fixed.

A first modification is described in FIG. 7. FIG. 7 is a partial side view of the ultrasound flaw detection device to which a float 28 is attached. The power supply unit 19 and the centering member 27 of the ultrasound flaw detection device are not shown in the drawing.

The flat 28 generates buoyancy in the water flow 39 so that the waterproof member housing the ultrasound flaw detector does not sink in the water, thereby preventing resistance caused by friction of the waterproof member 20 with the tube 38. The float 28 may be, for instance, a container which is made of material with a lower specific gravity than water and having air sealed inside, or a container made of lightweight wood material.

The float 28 is attached to one of the waterproof member 20 and the flexible shaft 25. Preferably, the float 28 is attached to a side of the flexible shaft 25 to avoid the diameter of the waterproof member 20 being larger. It is also preferable to attach the float 28 on an upstream side in a direction of the water flow 39. In this manner, the float 28 is provided on the upstream side so as to avoid the waterproof member 20 on a downstream side being pressed against the tube wall 38 by the pressure of the water flow and to allow the ultrasound flaw detection device to move smoothly in the tube 38. The float 28 is preferably kept approximately centered in the radial direction of the tube 38 and preferably attached near the ultrasound probe 11, or near the battery 18 which is heavy in weight.

In this manner, the float 28 which generates buoyancy in the water flow is attached to the flexible shaft 25 so as to minimize the influence of weight of the ultrasound flaw detector. As a result, the ultrasound flaw detection device can move smoothly in the tube 38.

Second Modification

Figure 8:
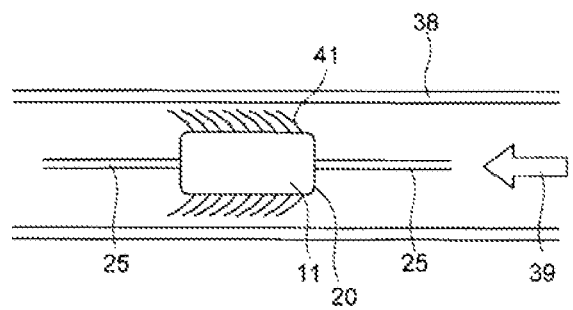
FIG. 8 is a partial side view of the ultrasound flaw detection device to which a whisker-shaped member is fixed.

FIG. 8 is a partial side view of the ultrasound flaw detection device of the immersion-type with a whisker-shaped member 41. The ultrasound flaw detection device has the whisker-shaped member 41 on a surface of the waterproof member 20 along the direction of the water flow 39. The whisker-shaped member 41 is preferably made of material with a lower specific gravity than water, such as carbon fiber. The whisker-shaped member 41 may be implanted in or attached to the waterproof member 20. The length of the whisker-shaped member 42 is not limited as long as it increases resistance to the water flow 39. The whisker-shaped member 41 is preferably fixed to the waterproof member 20 which houses the ultrasound probe 11. By this, the ultrasound probe 11 is kept approximately centered in the radial direction of the tube 38.

In this manner, the whisker-shaped member 14 is attached to the surface of the waterproof member 20 to increase resistance to the water flow 39. As a result, the ultrasound flaw detection device of the immersion-type can travel smoothly in the tube. Further, the whisker-shaped member 41 is brought into contact with the tube wall 38 so as to keep the waterproof member 20 approximately centered in the radial direction of the tube 38 and to prevent the friction resistance between the waterproof member 20 and the tube 38.

Third Modification

Figure 9:
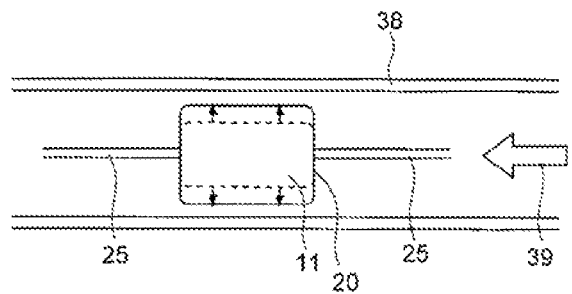
FIG. 9 is a partial side view of the ultrasound flaw detection device whose waterproof member has an enlarged outer diameter.

FIG. 9 illustrates a third modification and shows a partial side view of the ultrasound flaw detection device of the immersion-type provided with the waterproof member 20 with increased diameter. The outer diameter of the waterproof member 20 is increased in a cross-sectional plane perpendicular to the direction of the water flow 39. For instance, when the waterproof member 20 is formed into a round shape or an oval shape, the diameter of the waterproof member 20 is increase toward the tube wall 38. When the waterproof member 20 is formed into a polygonal column shape, the diameter of the waterproof member 20 is as large as possible to pass through the bending section in the tube 38.

At least one of the waterproof members 20 has the increased diameter. Preferably, the outer diameter of the waterproof member 20 housing the ultrasound probe 11 is increased. By this, the ultrasound probe 11 can be kept approximately centered in the radial direction of the tube 38.

In this manner, by increasing the outer diameter of the waterproof member 20, the waterproof member is subjected to greater pressure of the water flow 39. As a result, the ultrasound flaw detection device of the immersion-type can move smoothly in the tube 38.

Fourth Modification

Figure 10:
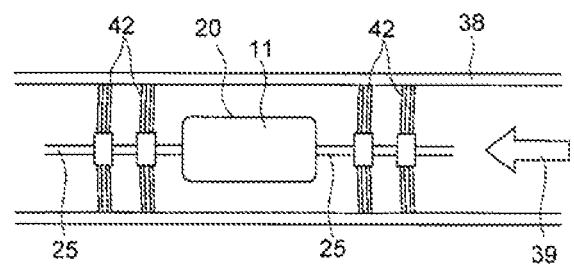
FIG. 10 is a partial side view of the ultrasound flaw detection device having a centering member.
Figure 25:
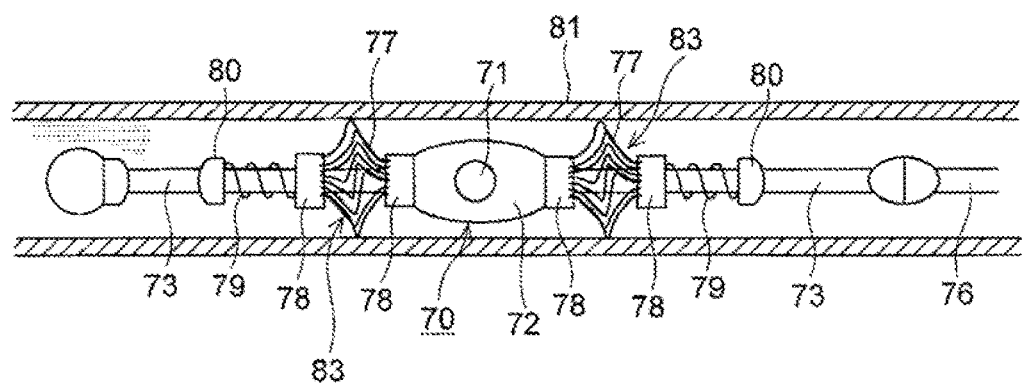
FIG. 25 is a side view of a conventional ultrasound flaw detection device.
Figure 26:
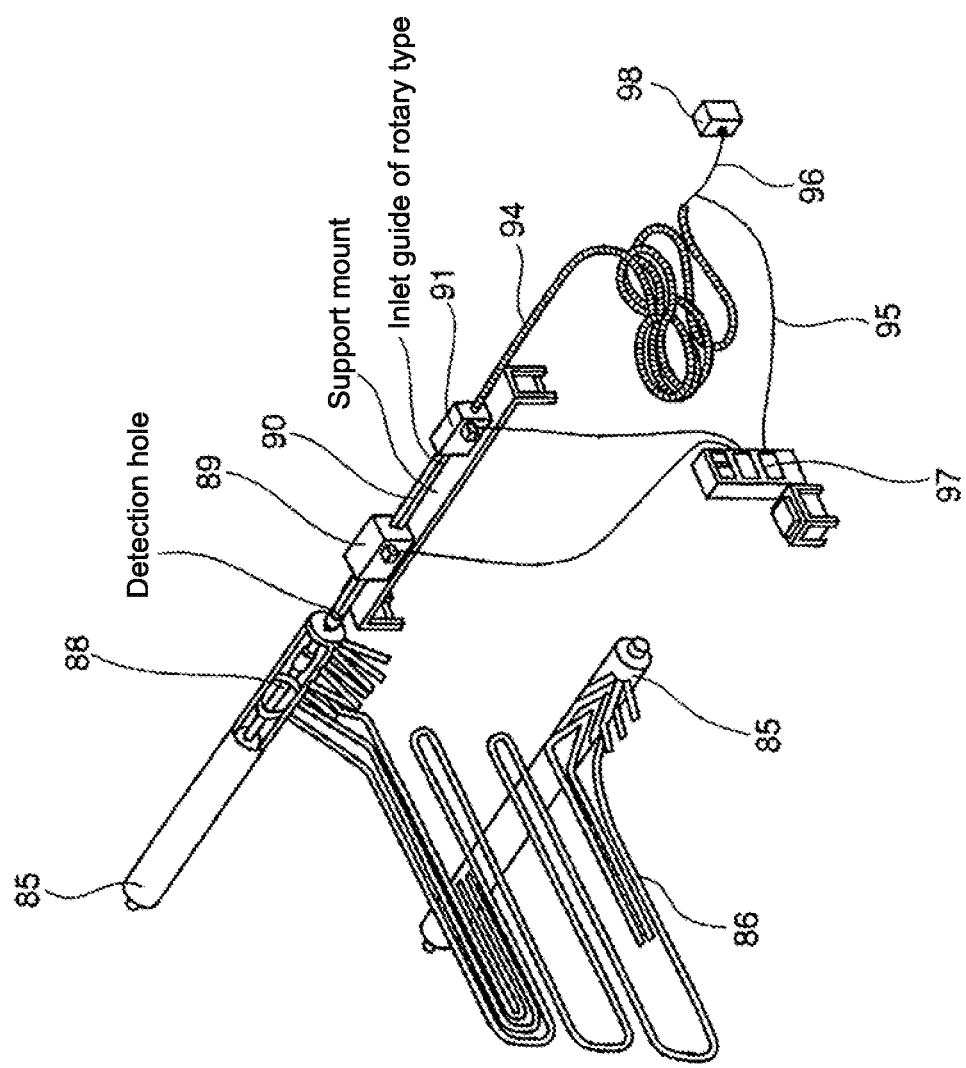
FIG. 26 illustrates a case where the conventional ultrasound flaw detection device is applied to a boiler tube.

FIG. 10 illustrates a fourth modification and is a partial side view of the ultrasound flaw detection device provided with a centering member 42. The ultrasound flaw detection device is provided with a plurality of centering members 42 to keep the ultrasound probe 11 approximately centered in the radial direction of the tube 38. Further, the resistance to the water flow 39 is increased by increasing a total pressure of the water flow to which the centering members 42 are subjected. The centering member 42 may be elastic wire extending radially from the flexible shaft 25 as shown in FIG. 10, or elastic wires installed to the flexible shaft 25 and the waterproof member 20 with an inclination angle as shown in FIG. 25.

In this manner, the pressure of the waterproof is increased by providing the plurality of centering members 42. As a result, the ultrasound flaw detection device of the immersion-type can move smoothly in the tube 38.

Fifth Modification

Figure 11:
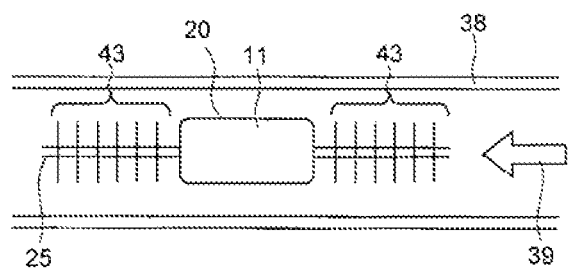
FIG. 11 is a partial side view of the ultrasound flaw detection device having a disk.

FIG. 11 illustrates a fifth modification and is a partial side view of the ultrasound flaw detection device provided with disks 43. The ultrasound flaw detection device of the immersion-type has the disks 43 installed to the flexible shaft 25. The disk 43 has a surface that is parallel or approximately parallel to a vertical surface to the direction of the water flow 39. More than one disk 43 may be installed to the flexible shaft 25. Different from the centering member 42, the diameter of the disk 43 must be set not greater than the largest diameter that passes through the bending section in the tube 38. The surface area that is subjected to the pressure of the water flow inevitably becomes smaller. However, the resistance to the pressure of the water flow can be increased by providing a plurality of the disks 43. As a result, the ultrasound flaw detection device of the immersion-type can move smoothly in the tube 38.

Sixth Modification

Figure 12:
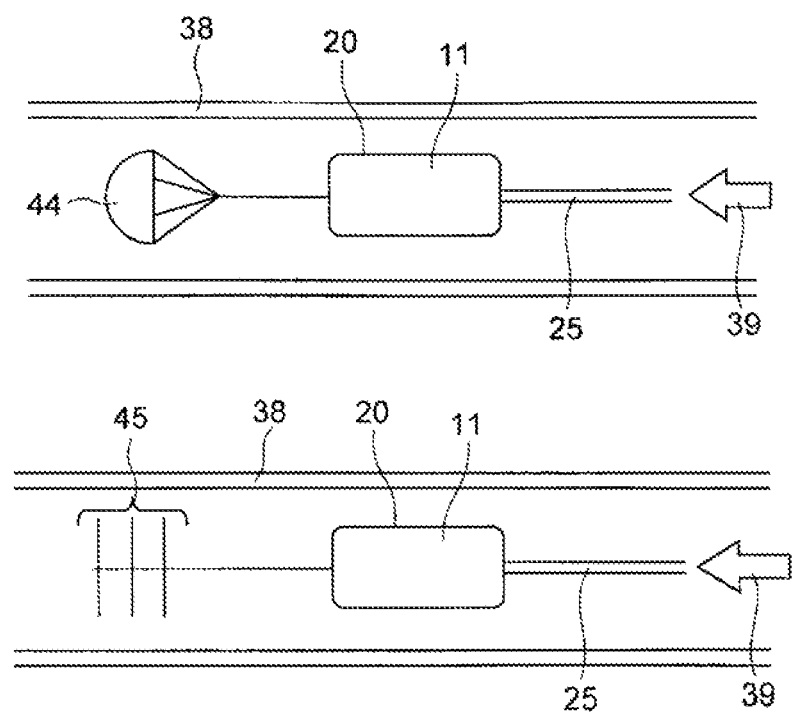
FIG. 12 is a partial side view of the ultrasound flaw detection device having a parachute-shaped member or a disk.

FIG. 12 illustrates a sixth modification and is a partial view of the ultrasound flaw detection device of the immersion-type provided with one of a parachute-shaped member 44 and a disk 45. The ultrasound flaw detection device is provided with the parachute-shaped member 44 or the disk 45 that is made of a material with a low specific gravity and formed such as to keep its shape. The parachute-shaped member 44 or the disk 45 is arranged on the most downstream side in the direction of the water flow 39 and is connected by means of a strip-shaped member such as light-weight wire or the like so as to utilize the pressure of the water flow.

In the manner similar to the fifth modification and different from the centering member 42, the diameter of the parachute-shaped member 44 and the disk 45 must be set not greater than the largest diameter that passes through the bending section in the tube 38. In the case of the parachute-shaped member 44, the parachute-shaped member 44 captures the water flow significantly, thereby increasing resistance to the water flow 39. Meanwhile, by providing a plurality of the disks 45 in a manner similar to the fifth modification, the resistance to the water flow 39 is increased. As a result, the ultrasound flaw detection device of the immersion-type can move smoothly in the tube 38.

Seventh Modification

Figure 13:
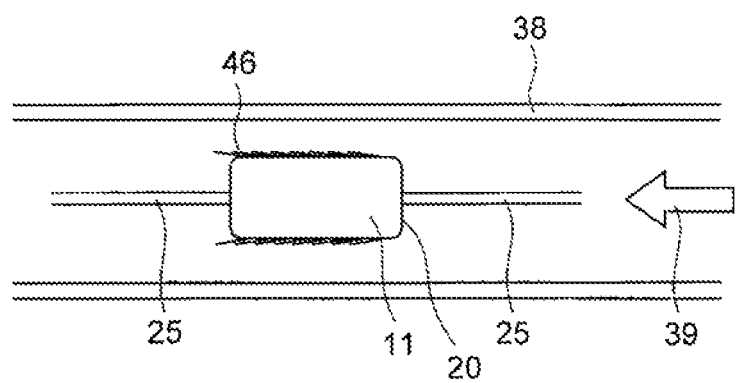
FIG. 13 is a partial side view of the ultrasound flaw detection device having a flow disturbing member which disturbs a water flow.

FIG. 13 illustrates a seventh modification and is a partial view of the ultrasound flaw detection device of the immersion-type provided with a flow-disturbing member 46. The flow-disturbing member 46 is a form of sheet that disturbs the water flow and adhered to the surface of the waterproof member 20. The flow-disturbing member 46 is a sheet-like member with a rough surface like a blanket and disturbs the water flow 39 to increase the resistance to the water flow.

The flow-disturbing member 46 may be shaped like a clothes brush having bristles implanted in a cloth-like member. The flow-disturbing member 46 is attached to the surface of the waterproof member 20 so as to disturb the water flow 39. This causes a part of the water flow 39 to be stirred near the waterproof member 20 and the stirred part of the water flow acts as resistance to the main water flow 39 to push the ultrasound flaw detection device. As a result, the ultrasound flaw detection device of the immersion-type can move smoothly in the tube 38.

Eighth Modification

Figure 14:
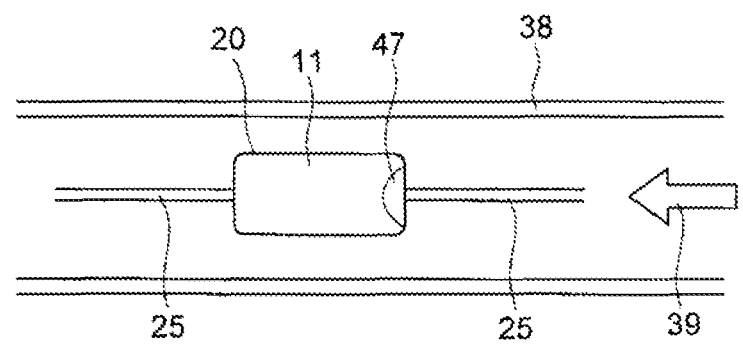
FIG. 14 is a partial side view of the ultrasound flaw detection device having a dent.

FIG. 14 illustrates an eighth modification and is a partial view of the ultrasound flaw detection device of the immersion-type provided with a dent 47. The ultrasound flaw detection device is provided with the dent 47 on a side of the waterproof member 20 that the water flow 39 hits.

In a manner similar to the case of the parachute-shaped member 44, by providing the dent 47 on the side that the water flow 39 hits, the water flow 39 is stirred (captured) significantly, thereby increasing the pressure difference and increasing the pressure of the water flow. As a result, the ultrasound flaw detection device of the immersion-type can move smoothly in the tube 38.

Ninth Modification

Figure 15:
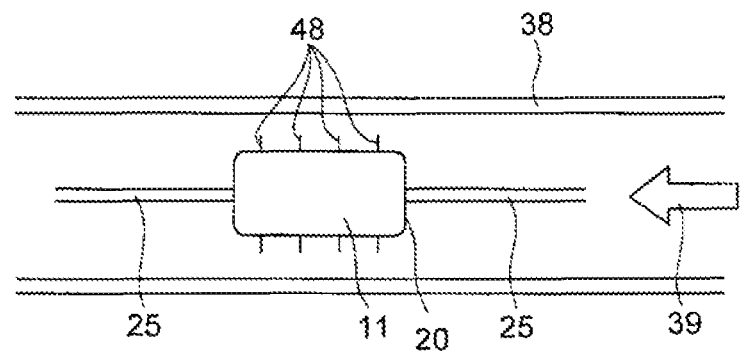
FIG. 15 is a partial side view of the ultrasound flaw detection device having an uneven part.

FIG. 15 illustrates a ninth modification and is a partial view of the ultrasound flaw detection device of the immersion-type provided with an uneven part 48. The ultrasound flaw detection device is provided with the uneven part 48 on the surface of the waterproof member 20 along the direction of the water flow 39 so as to generate pressure of the water flow.

The uneven part 48 may be, for example, disk-shaped members as shown in the drawing, or uneven part formed on the waterproof member 20. The structure of the uneven part 48 is not limited as long as it draws the water flow in and generates a hydraulic force. As a result, the ultrasound flaw detection device of the immersion-type can move smoothly in the tube 38.

Tenth Modification

Figure 16:
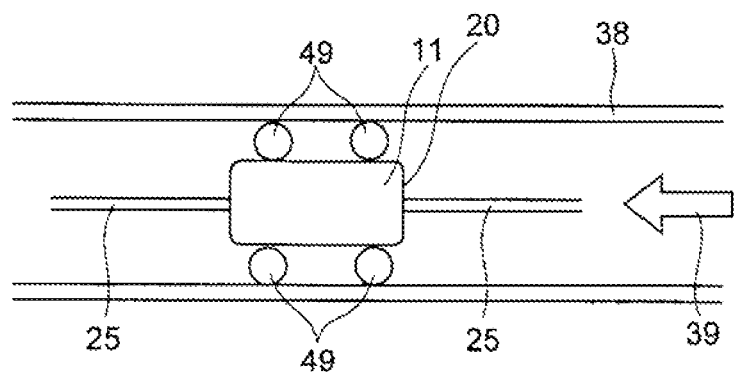
FIG. 16 is a partial side view of the ultrasound flaw detection device having a friction-reducing member.

FIG. 16 illustrates a tenth modification and is a partial view of the ultrasound flaw detection device of the immersion-type provided with a friction-reducing member 49. The ultrasound flaw detection device is provided with the friction-reducing-member 49 on a side of the waterproof member 20 that faces the tube wall 38. The friction-reducing member 49 reduces friction coefficient that occurs when the waterproof member 20 comes in contact with the tube wall 38. For instance, the friction-reducing member 49 may be a rotary member of a wheel type, a rotary member of a bearing type, a stationary member with small friction coefficient such as fluorine resin or the like.

By providing the friction-reducing member 49, only small friction resistance is generated when the waterproof member 20 comes in contact with the tube wall 38. As a result, the ultrasound flaw detection device of the immersion-type can move smoothly in the tube 38.

Eleventh Modification

FIG. 17 through FIG. 24 illustrate an eleventh modification and is a partial view of the ultrasound flaw detection device of the immersion-type provided with a position-information recognition unit. In the eleventh modification, an exemplary case of detecting the boiler tube 38 is explained.

Figure 17:
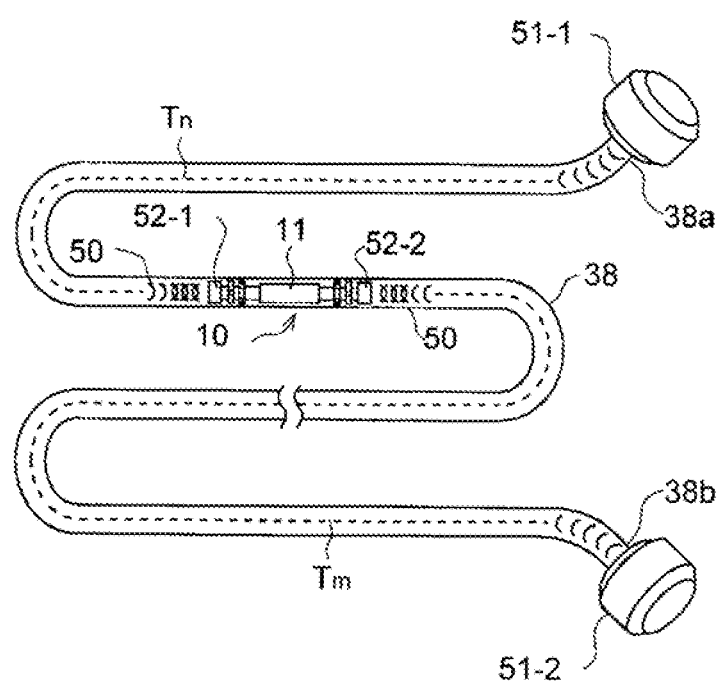
FIG. 17 is an overall view of the ultrasound flaw detection device having a position information recognition unit.
Figure 18:
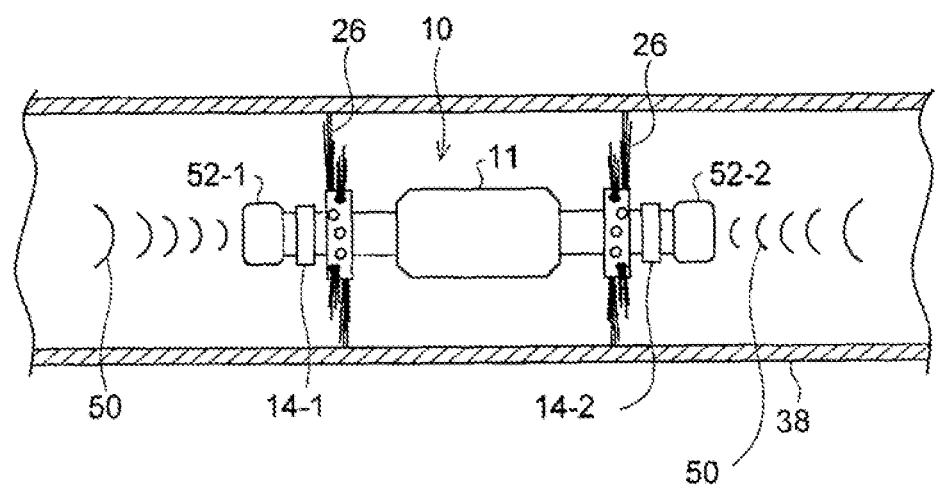
FIG. 18 is a partial view of the ultrasound flaw detection device having a position information recognition unit.

As shown in FIG. 17, sound wave transmitters 51-1 and 51-2 for transmitting sound wave 50 are provided at both an inlet 38a and an outlet 38b of the boiler tube 38. As shown in FIG. 17 and FIG. 18, a front-side receiver 52-1 and a rear-side receiver 52-2 are provided on the front side (a left side in the drawing) and the rear side (a right side in the drawing) of the ultrasound probe 11 respectively so as to receive the sound wave 50 from the sound wave transmitters 51-1 and 51-2.

Time data of receiving the sound wave 50 is stored in the memory units 14-1, 14-2. After measuring, the result is matched with the wall thickness data to determine the position.

The elastic wires shown in FIG. 10 are used as the centering member 26 to keep the ultrasound probe 11 centered in the radial direction of the boiler tube 38.

However, this is not limitative.

FIG. 19 shows the sound wave transmitter 51-2 being installed to an end 38b of the boiler tube 38 via an insertion nozzle 55.

In the eleventh modification, a pair of memory units 14-1 and 14-2 is provided to independently store the time data for the front side and the rear side respectively. This is not limitative, and it is also possible to use one memory unit to store the time data for both the front and rear sides.

In this manner, it is possible to determine a measuring position from a time difference obtained from the received sound wave 50. Specifically, the sound wave transmitters 51-1 and 51-2 simultaneously transmit sound waves 50 and the front-side receiver 52-1 and the rear-side receiver 52-2 receive the sound waves 50. The time data are stored in the memory units 14-1 and 14-2.

An exemplary method of obtaining position information is explained hereinafter.

Figure 22:
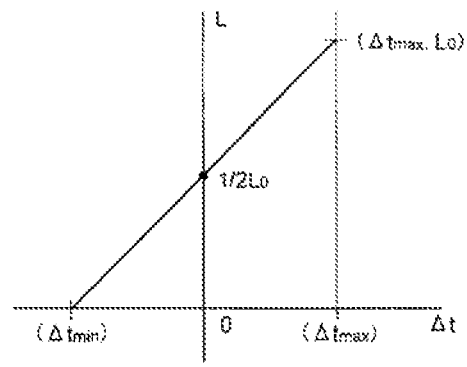
FIG. 22 is a graph that is used to obtain the position information.

FIG. 20 is a frame format of sound wave information and received signal information in relation to the eleventh modification. FIG. 21 is a diagram showing reception results and measuring positions. FIG. 22 is a graph that is used to obtain the position information in relation to the eleventh modification.

First, each of the sound wave transmitters 51-1 and 51-2 provided at both ends of the boiler tube 38 transmits a sound wave 50 every second. The transmitted sound wave, as shown in FIG. 20, is stored in the memory unit 14-1 as received signal information (T1, T3, . . . Tm) of the front-side receiver 52-1 and also stored in the memory unit 14-2 as received signal information (T2, T4, . . . Tn) of the rear-side receiver 52-2.

As a result, the time data shown in FIG. 21 are stored for the front-side receiver 52-1 and the rear-side receiver 52-2.

When $\Delta t$ is zero, a measured position is halfway in the entire length of the boiler tube 38. When $\Delta t$ is the smallest or greatest, the measured position is at full length of the boiler tube 38. This relationship is shown in FIG. 21 and FIG. 22.

After completing the detection, the data of times of receiving the sound waves 50 and the wall thickness measuring data are matched to determine a position where flaws, wall thicknesses and the like of the boiler tube 38 are detected.

Figure 23:
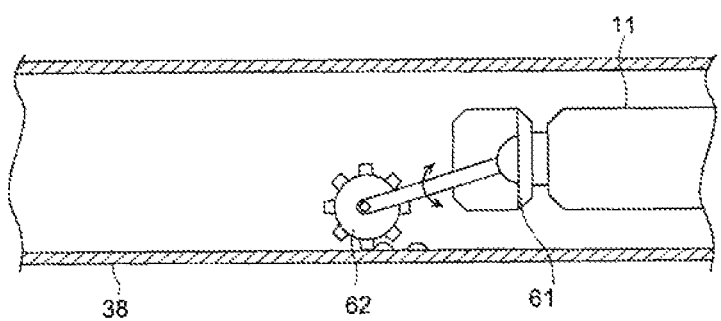
FIG. 23 is a partial side view of the ultrasound flaw detection device having a memory-equipped encoder.

As show in FIG. 23, a memory-equipped encoder 61 may be provided on a front end of the ultrasound probe 11 as a modified example of the position information recognition unit of the eleventh modification. The memory-equipped encoder 61 measures by allowing a wheel member 62 of a roller type to contact the inner periphery of the tube 38.

In such case, the wheel member having projections that correspond with projections formed on the inner periphery of the tube 38 so as to reduce contact friction between the wheel member and the inner periphery of the tube 38.

A distance can be obtained from a rotation speed of the wheel member 62, and the obtained distance is stored in a memory unit in the device. As a result, it is possible to determine the measuring position.

Figure 24:
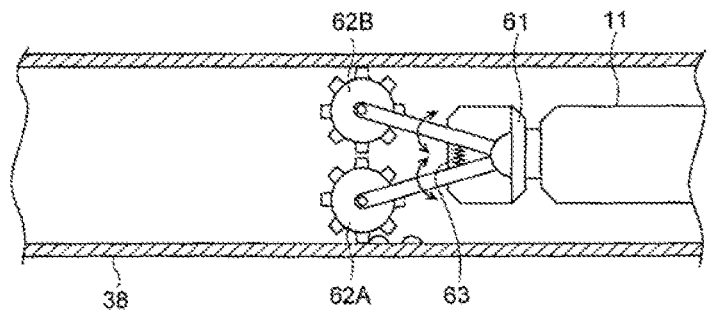
FIG. 24 is a partial side view of the ultrasound flaw detection device having another memory-equipped encoder different from the memory-equipped encoder of FIG. 23.

As shown in FIG. 24, a pair of wheel members of roller type 62A and 62B may be installed in both directions to improve traveling stability.

A spring may be installed as well to keep the wheel members 62A and 62B in contact with the inner periphery of the tube 38 by applying light pressure.

The ultrasound flaw detection device of the immersion-type in relation to the above preferred embodiments is configured such that the plurality of divided parts of the ultrasound flaw detector are housed in the waterproof members 20 that are connected with one another by the flexible shaft 25 and the ultrasound probe 11 is kept approximately centered in the radial direction of the tube 38 by the centering member 26. As a result, the ultrasound flaw detection device can travel smoothly in the tube 38 only with the pressure of the water flow and a cable for supplying electric power to the ultrasound probe or receiving and sending signals as well as a cable for moving the probe in the tube is no longer needed, thereby removing a shipping cost for the cables or a large pump or the like. This results in cost reduction. Further, it is possible to save space for installing the winding unit, the large pump or the like. The handling of the device is easier and thus, it is easier to maintain the device and the number of skilled workers can be downsized.

Without cables using a coil spring or the like for supplying electric power or sending and receiving signals, it is possible to reduce contact resistance at the bending sections of the tube. Further, by providing the float 28, the weight of the ultrasound flaw detector is canceled. By providing a structure or a member to be subjected to the pressure of the water flow more, or by providing the friction reducing member to reduce the friction between the waterproof member 20 and the tube wall 38, the ultrasound flaw detection device of the immersion-type can travel smoothly in the tube.

The ultrasound flaw detection device of the immersion-type and the ultrasound flaw detection system in relation to the preferred embodiments are preferably used in a boiler tube of the boiler installed in a thermal power plant or the like. The ultrasound flaw detection device of the preferred embodiments can be downsized and thus, it is possible to perform ultrasound flaw detection precisely and smoothly in a long boiler tube with small tube diameter.

The invention claimed is:

1. An ultrasound flaw detection device that is insertable in a tube to detect abnormalities within the tube while being moved in the tube by pressure of water flow, the device comprising:
  an ultrasound flaw detector which is divided into a plurality of parts and comprises:
    an ultrasound probe configured to emit an ultrasound wave from an inside of the tube to a tube wall and receive an echo signal to be received that is reflected from the tube wall;
    a pulser-receiver configured to transmit a pulse signal to the ultrasound probe and to which the received echo signal is inputted from the ultrasound probe;
    a memory unit configured to store the received echo signal inputted to the pulser-receiver;
    a control unit configured to control a transmitting timing of the pulse signal from the pulser-receiver to the ultrasound probe and control writing of the received echo signal to the memory unit;
    a power supply unit configured to supply power to the pulser-receiver;
  a plurality of waterproof members configured to house the plurality of parts of the ultrasound flaw detector, respectively;
  a plurality of flexible members interconnecting the plurality of waterproof members; and
  at least one centering member fixed directly on one of the flexible members,
  wherein a radial length of the centering member is smaller than an inner diameter of the tube so as to extend radially toward the tube wall outside of the plurality of waterproof members, the at least one centering member being configured as a plate member to receive the pressure of water flow and to keep the ultrasound probe approximately centered within the tube, and
  wherein the radial length of the at least one centering member is greater than a radial lengths of plurality of waterproof members so that an outer end of the at least one centering member is disposed radially outside of the plurality of waterproof members.

2. The ultrasound flaw detection device according to claim 1,
  wherein the ultrasound probe comprises a plurality of transducers that are arranged in a circumferential direction of the tube, and
  wherein the pulser-receiver is configured to transmit the pulse signal to the plurality of transducers with time interval.

3. The ultrasound flaw detection device according to claim 1, wherein the ultrasound flaw detector comprises an A/D conversion unit configured to perform A/D conversion of the received echo signal inputted to the pulser-receiver.

4. The ultrasound flaw detection device according to claim 3, wherein the control unit is a Field Programmable Gate Array configured to control the transmitting timing of the pulse signal from the pulser-receiver to the ultrasound probe and control the writing of the received echo signal to the memory unit.

5. The ultrasound flaw detection device according to claim 1, further comprising:
  a float which is fixed to the plurality of waterproof members and configured to generate buoyancy in the water flow.

6. The ultrasound flaw detection device according to claim 1, further comprising:
  a whisker-shaped member which is installed to a surface of the ultrasound flaw detector that is along a direction of the water flow.

7. The ultrasound flaw detection device according to claim 1, further comprising:
  a disk which is installed between a pair of the waterproof members that are disposed adjacent to one another, the disk being positioned perpendicularly relative to a direction of the water flow.

8. The ultrasound flaw detection device according to claim 1, further comprising:

one of a parachute-shaped member and a disk which is connected to one of the divided parts of the ultrasound flaw detector by means of a strip-shaped member, said one of the divided parts of the ultrasound flaw detector being arranged most downstream in a direction of the water flow.

9. The ultrasound flaw detection device according to claim 1, wherein the at least one centering member is disposed at a position that is closer to the waterproof member than a middle point of the flexible member connected to the waterproof member that houses the ultrasound probe.

10. An ultrasound flaw detection system comprising:
i) an ultrasound flaw detection device that is inserted in a tube and detects abnormalities within the tube while being moved in the tube by pressure of water flow, the ultrasound flaw detection device comprising:
an ultrasound flaw detector which is divided into a plurality of parts and comprises:
an ultrasound probe configured to emit an ultrasound wave from an inside of the tube to a tube wall and receive an echo signal to be received that is reflected from the tube wall;
a pulser-receiver configured to transmit a pulse signal to the ultrasound probe and to which the received echo signal is inputted from the ultrasound probe;
a memory unit configured to store the received echo signal inputted to the pulser-receiver;
a control unit configured to control a transmitting timing of the pulse signal from the pulser-receiver to the ultrasound probe and control writing of the received echo signal to the memory unit;
a power supply unit configured to supply power to the pulser-receiver;
a plurality of waterproof members configured to house the plurality of parts of the ultrasound flaw detector;
a plurality of flexible members interconnecting the plurality of waterproof members; and
at least one centering member fixed directly on one of the flexible members so as to extend radially toward the tube wall outside of the plurality of the waterproof members, the at least one centering member being configured as a plate member to receive the pressure of water flow and to keep the ultrasound probe approximately centered within the tube, wherein a radial length of the at least one centering member is greater than radial lengths of the plurality of waterproof members so that an outer end of the at least one centering member is disposed radially outside of the plurality of waterproof members;
ii) an interface unit which is arranged outside of the pipe and is permitted to connect to the memory unit of the ultrasound flaw detection device; and
iii) an output unit configured to output an abnormality detection result of the inside of the tube based on information received from the memory unit via the interface unit,
wherein the radial length of the centering member is smaller than an inner diameter of the tube.

11. The ultrasound flaw detection system according to claim 10,
wherein the ultrasound flaw detection device further comprises a calculation unit configured to calculate a wall thickness of the tube wall from a time difference between a first received echo signal reflected from an inner periphery of the tube wall and a second received echo signal reflected from an outer periphery of the tube wall, and
wherein the wall thickness of the tube wall having been calculated in the calculation unit is configured to be stored in the memory unit, and the stored wall thickness is configured to be outputted by the output unit via the interface unit.

12. The ultrasound flaw detection system according to claim 11,
wherein the ultrasound flaw detector comprises a plurality of transducers that are arranged in a circumferential direction of the tube wall, and the memory unit is configured to store the wall thickness of the tube wall for each of said plurality of transducers, and
wherein a smallest value of the wall thicknesses at a plurality of points that corresponds to said plurality of transducers is configured to be selected, and the selected smallest value is configured to be outputted corresponding to a position in a longitudinal direction of the tube.

13. The ultrasound flaw detection system according to claim 10, further comprising:
a signal processing unit configured to receive from the memory unit via the interface unit a first received echo signal that is reflected from an inner periphery of the tube wall and a second received echo signal reflected from an outer periphery of the tube wall, and calculate a wall thickness of the tube wall from a time difference between the first received echo signal and the second received echo signal,
wherein the wall thickness of the tube wall having been calculated in the signal-processing unit is configured to be outputted by the output unit.

14. The ultrasound flaw detection system according to claim 11, further comprising:
a noise-processing unit configured to exclude a wall thickness that corresponds to the first received echo signal that exceeds a threshold value that is set in advance.

15. The ultrasound flaw detection system according to claim 11, wherein a position in a longitudinal direction of the tube wall that corresponds to the wall thickness is configured to be determined from a measuring time of the received echo signal based on a reference echo signal at a characterizing part of the tube wall.

16. The ultrasound flaw detection system according to claim 10, wherein the output unit is configure to:
obtain reference echo signals corresponding to a characterizing part of the tube wall from the echo signal received from the memory unit via the interface unit;
calculate a position of the ultrasound flaw detector in the longitudinal direction based on a reference position corresponding to the reference echo signals by using a traveling speed of the ultrasound flaw detector; and
output the abnormality detection result with the position of the ultrasound flaw detector in the longitudinal direction.

* * * * *